United States Patent
McKenna et al.

(10) Patent No.: US 7,867,193 B2
(45) Date of Patent: Jan. 11, 2011

(54) DRUG DELIVERY APPARATUS

(75) Inventors: Michael J. McKenna, Southborough, MA (US); Jason O. Fiering, Cambridge, MA (US); Mark J. Mescher, West Newton, MA (US); Sharon G. Kujawa, Bedford, MA (US); William F. Sewell, Sherborn, MA (US); Anthony A. Mikulec, St. Louis, MO (US)

(73) Assignees: The Charles Stark Draper Laboratory, Inc., Cambridge, MA (US); Massachusetts Eye and Ear Infirmary, Boston, MA (US)

( * ) Notice: Subject to any disclaimer, the term of this patent is extended or adjusted under 35 U.S.C. 154(b) by 893 days.

(21) Appl. No.: 11/046,540

(22) Filed: Jan. 28, 2005

(65) Prior Publication Data
US 2006/0030837 A1 Feb. 9, 2006

Related U.S. Application Data

(60) Provisional application No. 60/540,283, filed on Jan. 29, 2004, provisional application No. 60/602,691, filed on Aug. 19, 2004.

(51) Int. Cl.
*A61M 29/00* (2006.01)
*A61M 37/00* (2006.01)
*A61M 31/00* (2006.01)
*A61N 1/30* (2006.01)

(52) U.S. Cl. .................. 604/96.01; 604/93.01; 604/65; 604/20

(58) Field of Classification Search .............. 435/6, 435/252.3, 7.2, 69.1, 183, 190, 196, 325; 604/99.02, 103.02, 103.09, 93.01, 99.01, 604/890.1, 20, 509; 530/350, 300; 536/23.5, 536/23.4; 424/239.1
See application file for complete search history.

(56) References Cited

U.S. PATENT DOCUMENTS

| | | | |
|---|---|---|---|
| 3,386,469 | A | 6/1968 | Kelly |
| 4,034,759 | A | 7/1977 | Haerr |
| 4,152,098 | A | 5/1979 | Moody et al. |
| 4,181,245 | A | 1/1980 | Garrett et al. |
| 4,541,429 | A | 9/1985 | Prosl |
| 4,594,058 | A | 6/1986 | Fischell |
| 4,858,883 | A | 8/1989 | Webster |
| 4,944,487 | A | 7/1990 | Holtermann |

(Continued)

FOREIGN PATENT DOCUMENTS

EP 1331019 7/2003

(Continued)

OTHER PUBLICATIONS

International Search Report for PCT/US2005/002727 (5 pgs.).

(Continued)

*Primary Examiner*—Nicholas D Lucchesi
*Assistant Examiner*—Ian K Holloway
(74) *Attorney, Agent, or Firm*—Goodwin Procter LLP

(57) ABSTRACT

An implantable drug delivery apparatus for delivering a drug into a bodily fluid in a body cavity of a patient over a period of time, which includes a hollow member that defines at least one lumen for facilitating a unidirectional recirculating flow of a therapeutic fluid through the lumen. The fluid can contain a bodily fluid, such as, for example, perilymph, and a drug. The apparatus also includes a pump, for example a single unidirectional pump, to control the flow rate of the therapeutic fluid through the hollow member, and an interface member in communication with at least one lumen of the hollow member. The device thus allows for the controlled delivery of the therapeutic fluid to a predetermined location in the bodily cavity of the patient, such as, for example, a cochlea of a human ear.

34 Claims, 8 Drawing Sheets

U.S. PATENT DOCUMENTS

| | | | |
|---|---|---|---|
| 5,205,819 A | 4/1993 | Ross et al. | |
| 5,441,597 A | 8/1995 | Bonne et al. | |
| 5,476,446 A * | 12/1995 | Arenburg | 604/21 |
| 5,578,002 A * | 11/1996 | Slettenmark | 604/65 |
| 5,643,207 A | 7/1997 | Rise | |
| 5,725,363 A | 3/1998 | Bustgens et al. | |
| 5,750,015 A | 5/1998 | Soane et al. | |
| 5,759,014 A | 6/1998 | Van Lintel et al. | |
| 5,770,029 A | 6/1998 | Nelson et al. | |
| 5,779,868 A | 7/1998 | Parce et al. | |
| 5,839,467 A | 11/1998 | Saaski et al. | |
| 5,858,188 A | 1/1999 | Soane et al. | |
| 5,858,195 A | 1/1999 | Ramsey | |
| 5,880,071 A | 3/1999 | Parce et al. | |
| 5,895,372 A * | 4/1999 | Zenner et al. | 604/93.01 |
| 5,938,904 A | 8/1999 | Bader et al. | |
| 5,958,203 A | 9/1999 | Parce et al. | |
| 5,962,081 A | 10/1999 | Ohman et al. | |
| 5,971,355 A | 10/1999 | Biegelsen et al. | |
| 5,972,187 A | 10/1999 | Parce et al. | |
| 5,989,399 A | 11/1999 | Chu et al. | |
| 5,989,402 A | 11/1999 | Chow et al. | |
| 5,993,634 A | 11/1999 | Simpson et al. | |
| 6,001,229 A | 12/1999 | Ramsey | |
| 6,007,690 A | 12/1999 | Nelson et al. | |
| 6,010,607 A | 1/2000 | Ramsey | |
| 6,010,608 A | 1/2000 | Ramsey | |
| 6,017,434 A | 1/2000 | Simpson et al. | |
| 6,033,191 A | 3/2000 | Kamper | |
| 6,033,546 A | 3/2000 | Ramsey | |
| 6,033,628 A | 3/2000 | Kaltenbach et al. | |
| 6,042,709 A | 3/2000 | Parce et al. | |
| 6,042,710 A | 3/2000 | Dubrow | |
| 6,068,752 A | 5/2000 | Dubrow et al. | |
| 6,080,295 A | 6/2000 | Parce et al. | |
| 6,086,825 A | 7/2000 | Sundberg et al. | |
| 6,087,743 A | 7/2000 | Guckel et al. | |
| 6,093,296 A | 7/2000 | Soane et al. | |
| 6,103,199 A | 8/2000 | Bjornson et al. | |
| 6,110,343 A | 8/2000 | Ramsey et al. | |
| 6,113,768 A | 9/2000 | Fuhr et al. | |
| 6,120,666 A | 9/2000 | Jacobson et al. | |
| 6,123,316 A | 9/2000 | Biegelsen et al. | |
| 6,126,140 A | 10/2000 | Johnson et al. | |
| 6,126,804 A | 10/2000 | Andresen | |
| 6,132,579 A | 10/2000 | Edwards et al. | |
| 6,136,171 A | 10/2000 | Frazier et al. | |
| 6,153,073 A | 11/2000 | Dubrow et al. | |
| 6,176,991 B1 | 1/2001 | Nordman | |
| 6,193,866 B1 | 2/2001 | Bader et al. | |
| 6,198,966 B1 * | 3/2001 | Heruth | 604/20 |
| 6,207,031 B1 | 3/2001 | Adourian et al. | |
| 6,227,809 B1 * | 5/2001 | Forster et al. | 417/53 |
| 6,231,737 B1 | 5/2001 | Ramsey et al. | |
| 6,235,175 B1 | 5/2001 | Dubrow et al. | |
| 6,251,247 B1 | 6/2001 | Mitsuhashi et al. | |
| 6,254,754 B1 | 7/2001 | Ross et al. | |
| 6,261,430 B1 | 7/2001 | Yager et al. | |
| 6,261,431 B1 | 7/2001 | Mathies et al. | |
| 6,264,892 B1 | 7/2001 | Kaltenbach et al. | |
| 6,284,113 B1 | 9/2001 | Bjornson et al. | |
| 6,287,520 B1 | 9/2001 | Parce et al. | |
| 6,296,749 B1 | 10/2001 | Balch et al. | |
| 6,296,752 B1 | 10/2001 | McBride et al. | |
| 6,306,272 B1 | 10/2001 | Soane et al. | |
| 6,306,273 B1 | 10/2001 | Wainright et al. | |
| 6,341,758 B1 | 1/2002 | Shih et al. | |
| 6,342,142 B1 | 1/2002 | Ramsey | |
| 6,375,817 B1 | 4/2002 | Taylor et al. | |
| 6,386,780 B1 | 5/2002 | Brummernhenrich et al. | |
| 6,406,605 B1 | 6/2002 | Moles | |
| 6,413,400 B1 | 7/2002 | Soane et al. | |
| 6,423,198 B1 | 7/2002 | Manz et al. | |
| 6,440,102 B1 | 8/2002 | Arenberg et al. | |
| 6,440,284 B1 | 8/2002 | Dubrow | |
| 6,448,090 B1 | 9/2002 | McBride | |
| 6,458,259 B1 | 10/2002 | Parce et al. | |
| 6,482,177 B1 * | 11/2002 | Leinders | 604/131 |
| 6,485,625 B1 | 11/2002 | Simpson et al. | |
| 6,527,003 B1 | 3/2003 | Webster et al. | |
| 6,540,895 B1 | 4/2003 | Spence et al. | |
| 6,547,942 B1 | 4/2003 | Parce et al. | |
| 6,561,224 B1 | 5/2003 | Cho | |
| 6,561,997 B1 | 5/2003 | Weitzel et al. | |
| 6,572,830 B1 | 6/2003 | Burdon et al. | |
| 6,582,576 B1 | 6/2003 | Chow et al. | |
| 6,592,733 B1 | 7/2003 | Foley et al. | |
| 6,635,226 B1 | 10/2003 | Tso et al. | |
| 6,659,982 B2 | 12/2003 | Douglas et al. | |
| 6,660,147 B1 | 12/2003 | Woudenberg et al. | |
| 6,685,697 B1 | 2/2004 | Arenberg et al. | |
| 6,752,914 B1 | 6/2004 | Hassard et al. | |
| 6,764,060 B2 | 7/2004 | Fukano et al. | |
| 6,773,567 B1 | 8/2004 | Wolk | |
| 6,808,609 B1 | 10/2004 | Soane et al. | |
| 6,824,663 B1 | 11/2004 | Boone | |
| 6,827,831 B1 | 12/2004 | Chow et al. | |
| 6,929,030 B2 | 8/2005 | Unger et al. | |
| 6,929,239 B1 | 8/2005 | Colin et al. | |
| 6,945,116 B2 | 9/2005 | Xie et al. | |
| 6,986,365 B2 | 1/2006 | Henning et al. | |
| 7,134,639 B2 | 11/2006 | Gilbert et al. | |
| 7,147,205 B1 | 12/2006 | Fischer et al. | |
| 7,192,001 B2 | 3/2007 | Wise et al. | |
| 7,232,109 B2 | 6/2007 | Driggs et al. | |
| 7,254,008 B2 | 8/2007 | Xie et al. | |
| 7,293,581 B2 | 11/2007 | Gilbert et al. | |
| 7,311,503 B2 | 12/2007 | Van Lintel et al. | |
| 2002/0048536 A1 | 4/2002 | Bergh et al. | |
| 2002/0098097 A1 | 7/2002 | Singh | |
| 2002/0127736 A1 | 9/2002 | Chou et al. | |
| 2002/0144738 A1 | 10/2002 | Unger et al. | |
| 2002/0166585 A1 | 11/2002 | O'Connor et al. | |
| 2002/0172969 A1 | 11/2002 | Burns et al. | |
| 2003/0071235 A1 | 4/2003 | Gamble et al. | |
| 2003/0127329 A1 | 7/2003 | DeVoe et al. | |
| 2003/0171738 A1 * | 9/2003 | Konieczynski et al. | 604/891.1 |
| 2003/0175947 A1 | 9/2003 | Liu et al. | |
| 2003/0196695 A1 | 10/2003 | O'Connor et al. | |
| 2003/0229336 A1 | 12/2003 | Jacobsen et al. | |
| 2004/0026461 A1 | 2/2004 | Bougamont et al. | |
| 2004/0036047 A1 | 2/2004 | Richter | |
| 2004/0053290 A1 | 3/2004 | Terbrueggen et al. | |
| 2004/0089357 A1 | 5/2004 | Dube et al. | |
| 2004/0127852 A1 | 7/2004 | Gray et al. | |
| 2004/0188648 A1 | 9/2004 | Xie et al. | |
| 2005/0065584 A1 * | 3/2005 | Schiff et al. | 607/105 |
| 2005/0072946 A1 | 4/2005 | Studer et al. | |
| 2005/0116798 A1 | 6/2005 | Bintoro et al. | |
| 2005/0131332 A1 * | 6/2005 | Kelly et al. | 604/4.01 |
| 2005/0238506 A1 * | 10/2005 | Mescher et al. | 417/413.1 |
| 2006/0287689 A1 * | 12/2006 | Debruyne et al. | 607/57 |
| 2007/0200081 A1 | 8/2007 | Elizarov et al. | |
| 2007/0234785 A1 | 10/2007 | Beerling et al. | |
| 2008/0009836 A1 | 1/2008 | Fiering et al. | |

FOREIGN PATENT DOCUMENTS

| | | |
|---|---|---|
| WO | 95/20409 | 8/1995 |
| WO | WO-99/38552 | 8/1999 |
| WO | 02/11703 A1 | 2/2002 |
| WO | 03/034960 A1 | 5/2003 |
| WO | WO-03/075984 | 9/2003 |
| WO | WO-03/099351 | 12/2003 |

WO  WO-2007/024829  3/2007

OTHER PUBLICATIONS

Written Opinion of the International Searching Authority for PCT/US2005/002727 (6 pgs.).

International Search Report and Written Opinion for Application No. PCT/US07/017817 dated Jan. 18, 2008 (14 pages).

Brown et al. "Osmotic pump implant of drugs into the inner ear," Hearing Research 70 (1993) 167-172.

Cabuz et al. "MEMS-Based Flow Controller for Flow Cytometry" DARPA Contract MDA972-00-C-0029, 2 pgs.

Carvalho et al. "The Effect of Cochlesostomy and Intracochlear Infuction on Auditory Brain Stem Response Threshold in the Guinea Pig" The American Journal of Otology, 20:87-90 (1999).

Cousseau et al. "Improved Micro-Flow Regulator for Drug Delivery Systems" IEEE, 2001, 527- 530.

Fitch et al. "Pressure-Based Mass Flow Control Using Thermopneumatically-Actuated Microvalves" In Proceedings, Sensors and Actuators Workshop, pp. 162-165 (Transducers Research Foundation, Cleveland, OH (1998).

Hoffer et al. "Microdose Gentamicin Administration via the Round Window Microcatheter Results in Patients with Meniere's Disease" Annals New York Academy of Sciences, pp. 46-51.

International Search Report and Written Opinion for Application No. PCT/US08/001324 (21 pages), dated Sep. 30, 2008.

Langer "Drugs on Target" Science (2001) vol. 293, 58-59.

Laryngologica "Round Window Gentamicin -Catheter—a New Therapeutic Tool in Menier's Disease" Charabi, Samih (2000) 120:1, 108-110.

Lehner et al. "A Totally Implantable Drug Delivery SYstem for Local Therapy of the Middle and Inner Ear" ENT—Ear Nose & Throat Journal (1997) vol. 76, No. 8, 567-570.

Lintel et al. "A Piezoelectric Micropump Based on Micromachining of Silicon" Sensors and Actuators, 15 (1988) 153-167.

Mescher et al. "Surface Mount Microfluidic Flow Regulator on a Polymer Substrate" 7th International Conference on Miniaturized Chemical and Biochemical Systems, Oct. 5-9, 2003, Squaw Valley, CA, 947-950.

Paasche et al. "Technical Report: Modification of a Cohlear Implant Electrode for Drug Delivery to the Inner Ear" Ontology & Neurology (2003) 24:222-227.

Praetorius et al. "A Novel Microperfusion System for the Long-Term Local Supply of Drugs to the Inner Ear: Implantation and Function in the Rat Model" Audiol. Neurootol. (2001) 6:250-258.

Prieskorn et al. "technical report: chronic and acute intraochlear infusion in rodents" Elsevier, Hearing Research 140 (2000) 212-215.

Santini et al. "A controlled-release microchip" Nature, vol. 397, (1999) 335-338.

Schoendorf et al. "Continuous intratympanic infusion of gentamicin via a microcatheter in Meniere's disease" Otolaryngology-Head and Neck Surgery, vol. 124, No. 2 (2001) 203-207.

Shepherd et al. "A multichannel scala tympani electrode array incorporating a drug delivery system for chronic intracochlear infusion" Hearing Research 172 (2002) 92-98.

Smits "Piezoelectric Micropump with Three Valves Working Peristaltically" Sensors and Actuators, A21-A23 (1990) 206-206.

Sridhar et al. "Unique Postsynaptic Signaling at the Hair Cell Efferent Synapse Permits Calcium to Evoke Changes on Two Time Scales" The Journal of Neuroscience, (1997) 17(1):428-437.

Weibel, et al. "Torque-Actuated Valves for Microfluidics" Analytical Chemistry 77(15), 4276- 4733, Aug. 2005.

Yang et al. "Using Compliant Membranes for Dynamic Flow Stabilization in Microfluidic Systems" (2005) IEEE 706-709.

Yu et al. "Responsive biomimetic hydrogel valve for microfluidics" Applied Physics Letters, vol. 78, No. 17 (2001) 2589-2591.

Zengerle et al. "A bidirectional silicon micropump" Sensors and Actuators A 50 (1995) 81-86.

Dube et al. "26.1: A Si-Based FPW Sensor Array System with Polymer Microfluidics Integrated on a PCB" IEEE (2002) 460-465.

Gantz et al. "Combing Acoustic and Electric Hearing" Department of Otolaryngology-Head and Neck Surgery and Department of Speech and Pathology, University of Iowa, pp. 1-18.

Kingma et al. "Chronic drug infusion into the scala tympani" Journal of Neuroscience Methods, 45 (1992) 127-134.

Kujawa et al. "A nicotinic-like receptor mediates suppression of distortion product otaoacoustic emissions by contralateral sound" Elsevier Science B.V., Hearing Research 74 (1994) 122-134.

Madou et al. "Exploitation of a Novel Artificial Muscle for Controlled Drug Delivery" Department of Chemistry and Materials Sciecne and Engineering, Ohio State Univ. 495-497.

Miller et al. "Neurotrophins Can Enhance Spiral Ganglion Cell Survival after Inner Hair Cell Loss" Int. J. Devl. Neuroscience, (1997) vol. 15, No. 4/5, pp. 631-643.

* cited by examiner

| NAME | | | DESIGN VARIATIONS | | | |
|---|---|---|---|---|---|---|
| | | | MODE 1 | | MODE 2 | |
| DESIGN DESCRIPTION | SYM-BOL | UNITS | HIGH FLOW | LOW FLOW | LOW FLOW | HIGH FLOW |
| DESIGN INPUTS | | | MODE 1 IS A CONTINUOUS MODE, NO MODULATION OF THE PUMP SIGNAL | | MODE 2 USES MODULATION OF THE PUMP SIGNAL | |
| PUMP FREQUENCY | $f_p$ | Hz | 0.014 | 0.003 | 2 | 2 |
| PUMP CYCLE TIME (1/fp) | $t_c$ | sec | 71.3 | 337.7 | 0.5 | 0.5 |
| MODULATION TIME | $t_m$ | min | | | 1.19 | 5.63 |
| STROKE VOLUME | $V_{stroke}$ | uL | 0.5 | 0.5 | 0.5 | 0.5 |
| AVERAGE PUMP RATE | ISO | uL/min | 0.421 | 0.089 | 60 | 60 |
| PRIMARY FEED ID | $D_{IF}$ | mm | 1 | 2 | 1 | 2 |
| PRIMARY RETURN ID | $D_{IR}$ | mm | 1 | 2 | 1 | 2 |
| PRIMARY FEED OD | $D_{OF}$ | mm | 1.25 | 2.25 | 1.25 | 2.25 |
| PRIMARY RETURN OD | $D_{OR}$ | mm | 1.35 | 2.25 | 1.25 | 2.25 |
| PRIMARY FEED LENGTH | $L_F$ | cm | 50 | 50 | 50 | 50 |
| PRIMARY RETURN LENGTH | $L_R$ | cm | 50 | 50 | 50 | 50 |
| T FEED ID | $D_{IFT}$ | um | 75 | 75 | 75 | 75 |
| T RETURN ID | $D_{IRT}$ | um | 250 | 250 | 250 | 250 |
| T FEED LENGTH | $L_{FT}$ | mm | 50 | 10 | 50 | 10 |
| T RETURN LENGTH | $L_{RT}$ | mm | 50 | 10 | 50 | 10 |
| MIXER OUTPUT ID | $D_{IM}$ | um | 75 | 75 | 75 | 75 |
| MIXER OUTPUT LENGTH | $L_M$ | mm | 20 | 20 | 20 | 20 |

CONTINUE FROM FIG. 7A

| NAME | | | DESIGN VARIATIONS | | | |
|---|---|---|---|---|---|---|
| | | | MODE 1 | | MODE 2 | |
| DESIGN DESCRIPTION | SYM-BOL | UNITS | HIGH FLOW | LOW FLOW | LOW FLOW | HIGH FLOW |
| DESIGN INPUTS | | | MODE 1 IS A CONTINUOUS MODE, NO MODULATION OF THE PUMP SIGNAL | | MODE 2 USES MODULATION OF THE PUMP SIGNAL | |
| PRIMARY FEED RESISTANCE | $R_F$ | psi*min/uL | 3.94E-05 | 2.46E-06 | 3.94E-05 | 2.46E-06 |
| PRIMARY RETURN RESISTANCE | $R_R$ | psi*min/uL | 3.94E-05 | 2.46E-06 | 3.94E-05 | 2.46E-06 |
| T FEED RESISTANCE | $R_{FT}$ | psi*min/uL | 1.25E-01 | 2.49E-02 | 1.25E-01 | 2.49E-02 |
| T RETURN RESISTANCE | $R_{RT}$ | psi*min/uL | 1.01E-03 | 2.02E-04 | 1.01E-03 | 2.02E-04 |
| OUTPUT RESISTANCE | $R_M$ | psi*min/uL | 4.98E-02 | 4.98E-02 | 4.98E-02 | 4.98E-02 |
| FEED BUBBLE LENGTH | LFB | mm | 0.0 | 0.0 | 0.0 | 0.0 |
| FEED INITIAL BUBBLE PRESSURE | PFBO | psi*min/uL | 14.0 | 14.0 | 14.0 | 14.0 |
| AVERAGE OPER. BUBBLE PRESSURE (FEED) | PFBA | psi*min/uL | 14.0 | 14.0 | 14.0 | 14.0 |
| FEED BUBBLE CAPACITANCE | CFB | uL/psi | 0.0 | 0.0 | 0.0 | 0.0 |
| FEED TUBE COMPLIANCE CAPACITANCE | CFC | uL/psi | 2.1 | 16.5 | 2.1 | 16.5 |
| PRIMARY FEED CAPACITANCE | $C_F$ | uL/psi | 2.1 | 16.5 | 2.1 | 16.5 |
| RETURN BUBBLE LENGTH | LRB | mm | 0.0 | 0.0 | 0.0 | 0.0 |
| RETURN INITIAL BUBBLE PRESSURE | PRBO | psi | 14.0 | 14.0 | 14.0 | 14.0 |
| AVERAGE OPER. BUBBLE PRESSURE (RETURN) | PRBA | psi | 14.0 | 14.0 | 14.0 | 14.0 |
| RETURN BUBBLE CAPACITANCE | CRB | uL/psi | 0.0 | 0.0 | 0.0 | 0.0 |
| RETURN TUBE COMPLIANCE | CRC | uL/psi | 2.1 | 16.5 | 2.1 | 16.5 |
| PRIMARY RETURN CAPACITANCE | $C_R$ | uL/psi | 2.1 | 16.5 | 2.1 | 16.5 |
| MAXIMUM PUMP P | $P_{max}$ | psi | | | 7.5 | 1.5 |
| CYCLE VOLUME | $V_{cyc}$ | uL | -0.223 | -0.085 | -15.29 | -24.46 |
| MAXIMUM FLOW RATE | $f_{max}$ | uL/min | -0.390 | -0.040 | -26.75 | -10.15 |

FIG. 7B

DRUG DELIVERY APPARATUS

CROSS-REFERENCE TO RELATED APPLICATIONS

This application claims priority to and the benefit of U.S. provisional patent application Ser. No. 60/540,283, filed Jan. 29, 2004, and U.S. provisional patent application Ser. No. 60/602,691, filed Aug. 19, 2004, each application being incorporated herein by reference in its entirety.

FIELD OF THE INVENTION

The present invention relates generally to the field of drug delivery devices employing catheters and/or cannulas to transport fluid from a reservoir to a patient and, more particularly, to a device for introducing a drug into patient's bodily fluid, such as, for example, into perilymph in the human ear, as well as to methods for infusing drugs into cochlea for treatment of hearing loss and other disorders of hearing and vestibular function.

BACKGROUND OF THE INVENTION

Sensorineural hearing loss (SNHL) is common, and its impact on human communication, and quality of life, significant. It is estimated that some 28 million individuals in the United States suffer from hearing loss. As our population ages, hearing loss prevalence is expected to climb rapidly, nearly doubling by the year 2030. Causes range from degenerative processes associated with aging and genetic disorders to environmental exposure to loud sounds and toxic agents. Consequences range from moderate communication difficulty and social withdrawal to profound deafness and its significant challenges. At present, management of SNHL centers on the use of hearing aids and cochlear implants. However, such treatments cannot address hearing loss prevention, they cannot minimize heating loss progression and, even with optimal device fitting, cannot increase a damaged ear's basic capacity. As a result, many users continue to experience significant communication difficulties.

Recent advances in the pharmacology and molecular biology of hearing have revealed new and powerful possibilities for preventing or minimizing hearing loss. The crux of the problem in SNHL is loss of the delicate cochlear sensory cells that detect the exquisitely small mechanical vibrations associated with sound. In human ears, once lost or damaged, these sensory cells do not regenerate and this compromise is often followed by secondary degeneration of auditory neurons. However, scientists and clinicians are making rapid progress in understanding the molecular mechanisms associated with cochlear and auditory nerve degenerative processes. Additional insight into the molecular signals involved in generating new hair cells is rapidly accumulating, and with this insight comes the promise of novel and precise drug treatments. Moreover, the extraordinary progress that has been made in defining the genes involved in a number of human genetic forms of deafness offers hope for gene-transfer and molecular approaches to treat these diseases.

For therapies based on these discoveries to become clinically useful, it will be necessary to develop safe and reliable mechanisms for the delivery of complex compounds into the inner ear. Direct delivery to the fluids of the inner ear is necessary because of the presence of a blood-labyrinth drug barrier, which is anatomically and functionally similar to the blood-brain barrier. That is, through the presence of so-called 'tight junctions' between adjacent cells in the inner ear end organs, substances outside these organs encounter substantial physical barrier to entry, this protecting the delicate sensory structures within from insult. This 'protection', however, also prevents certain molecules with potentially therapeutic effect from gaining access to their inner ear targets. Prime candidates for exclusion from the cochlea after systemic injection are complex molecules, such as proteins and peptides, as well as any molecule that is not lipid soluble.

Current otologic practice requires drug delivery to the inner ear, but uses inefficient routes. Drugs are commonly delivered systemically, with the hope that they will find their way to their intended inner ear targets in the form and concentration desired and without serous side effects. Systemic corticosteroids, for example, are used in the otologic management of idiopathic sudden and immune-mediated sensorineural hearing losses. Their clinical usefulness, however, is limited by undesirable side effects arising from the high systemic doses required to achieve sufficient cochlear fluid levels of drug to produce the intended inner ear effects.

Local drug application by transtympanic perfusion of the middle ear with the goal of diffusion through the round window membrane (RWM) into the fluid spaces on the inner ear) was introduced nearly 50 years ago with aminoglycoside treatment of Meniere's disease. This method or some variant remains in common use in the treatment of inner ear diseases, notably the intractable vertigo that can be associated with Meniere's disease, but has been used as well for sudden sensorineural hearing loss, autoimmune inner ear disease, and even tinnitus for review. Accomplished as an office procedure, drug is injected through the tympanic membrane into the middle ear space. The patient then lies with the treated ear 'up' so that the drug has a better chance of making contact with the RWM, through which the drugs must diffuse to gain access to the inner ear. With the goal of extending the time of drug availability to the inner ear, newer methods of intratympanic drug delivery have employed several strategies to prolong drug contact with the RWM, including, placing absorbent material on or near the TWM and using pump-driven microcatheter systems.

Delivery of drugs to the middle ear reduces systemic side effect, but access to the inner ear is unpredictable. Middle ear application has advantages over systemic drug delivery, in that drugs so applied can reach their desired targets at higher concentrations and without unwanted systemic side effects. The application is straightforward, and complications are minimal. A major limitation of these methods, however, is the inability to precisely control the amount of drug that diffuses from the middle ear through the RWM into the inner ear. Individual variation in mucous membrane thickness, mucosal folds and middle ear anatomy can have a significant impact on the amount of drug that ultimately enters the inner ear. Some commentators, for example, report round window niche obstruction in 33% of human ears. This becomes even more problematic when considering delivery of coplex macromolecules with limited diffusion coefficients and those requiring sequenced delivery. Additionally, the bolus application used by certain existing systems makes them poorly suited for direct inner ear delivery. Although such devices may be useful for delivery of low molecular weight, stable, lipid soluble compounds like steroids, they would not be suitable for the delivery of the unstable macromolecules that ultimately will be the therapeutic compounds with greatest potential benefit.

Direct intracochlear drug delivery, which has been utilized successfully in animals, has significant potential advantages for therapeutic application. The practice of placing drugs of interest within cochlear perilymphatic spaces via a perfusion technique is a method with a long history of successful application. When carefully administered, the technique itself has been shown to have little effect on a variety of gross cochlear and neural potentials as recorded from sites within and near the cochlea. This mode of delivery bypasses the blood-cochlea barrier, allowing drugs to reach their intended targets more directly with lower doses and fewer non-specific actions. Drugs are largely unaltered by metabolic changes that inevitably occur with other routes of administration. Drugs perfused into the perilymph compartment of scala tympani have ready access to the hair cells and synaptic regions of hair cells, a view supported by investigations in which various stains demonstrated ready access to structures within the organ of Corti when introduced via the scala tympani perilymph compartment. Additionally, a comparison of the concentrations of cholinergic antagonists required to block the cochlear efferents in vivo and those effective at in vitro isolated outer hair cells shows remarkable close agreement.

Thus, in order to treat ear disorders, it may often be necessary to deliver therapeutic agents to various ear tissues in a controlled, safe, and efficient manner. For example, a variety of structures have been developed which are capable of delivering/administering therapeutic agents into the external auditory canal of the outer ear. U.S. Pat. No. 4,034,759 to Haerr discloses a hollow, cylindrical tube manufactured of sponge material, e.g. dehydrated cellulose, which is inserted into the external auditory canal of a patient. When liquid medicines are placed in contact with the tube, it correspondingly expands against the walls of the auditory canal. As a result, accidental removal of the tube is prevented. Furthermore, medicine materials absorbed by the tube are maintained in contact with the walls of the external auditory canal for treatment purposes.

However, as mentioned above, the delivery of therapeutic agents in a controlled and effective manner is considerably more difficult with respect to tissue structures of the inner ear (e.g. those portions of the ear surrounded by the otic capsule bone and contained within the temporal bone which is the most dense bone tissue in the entire human body). The same situation exists in connection with tissue materials, which lead into the inner ear (e.g. the round window membrane). Exemplary inner ear tissue structures of primary importance for treatment purposes include but are not limited to the cochlea, the endolymphatic sac/duct, the vestibular labyrinth, and all of the compartments (and connecting tubes) that include these components. Access to these and other inner ear tissue regions is typically achieved through a variety of structures, including but not limited to the round window membrane, the oval window/stapes footplate, the annular ligament, and the otic capsule/temporal bone, all of which shall be considered "middle-inner ear interface tissue structures" as described in greater detail below. Furthermore, as indicated herein, the middle ear shall be defined as the physiological air-containing tissue zone behind the tympanic membrane (e.g. the ear drum) and ahead of the inner ear.

The inner ear tissues listed above are of minimal size and only readily accessible through invasive microsurgical procedures. In order to treat various diseases and conditions associated with inner ear tissues, the delivery of drugs to such structures is often of primary importance. Representative drugs that are typically used to treat inner ear tissues include but are not limited to urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), antioxidants, neurotrophins, nerve growth factors, various therapeutic peptides, and polysaccharides. The treatment of inner eat tissues and/or fluid cavities may involve altering the pressure, volume, electrical activity, and temperature characteristics thereof. Specifically, a precise balance must be maintained with respect to the pressure of various fluids within the inner ear and its associated compartments. Imbalances in the pressure and volume levels of such fluids can cause various problems, including but not limited to conditions known as endolymphatic hydrops, endolymphatic hypertension, perilymphatic hypertension, perilymphatic hydrops, perilymphatic fistula, intracochlear fistula, Meniere's disease, tinnitus, vertigo, hearing loss related to hair cell or ganglion cell damage/malfunction, and ruptures in various membrane structures within the ear.

With respect to existing methods' of drug delivery, implantable and externally mounted drug infusers use a "one-way" infusion system where a reservoir empties into the tissue directly or through a catheter. To be pumped along a catheter, however, drugs must have appropriate physical properties. For example, it has been determined that dry compounds, which may be more stable than aqueous ones, cannot be used in a conventional infuser. In another example, it has been determined that highly concentrated compounds may be prohibited because of local reaction at the catheter outlet. Moreover, in the application to inner ear diseases, dosage to the relevant tissues of the cochlea can be difficult or impossible to assess and control by the methods described above, and no device has been provided for programmable long-term delivery, either to the middle eat or inner ear.

Known methods require a relatively complicated mechanism to achieve mixing and circulating flow between reservoir and patient. These more complicated methods include having two tubes entering the patient, rather than just one, or having a two-way pump, two pumps, or a switching valve at the pump.

For example, drugs are delivered to the inner ear by infusing the middle ear and allowing the medication to diffuse through the local tissue and into the inner ear. Alternatively drugs are given systemically (e.g., orally or by injection). For example, U.S. Pat. No. 5,895,372 to Zenner, incorporated by reference herein, discloses an implantable dosaging system that injects drugs into the middle ear using a manually operated pump. As another example, U.S. Pat. No. 6,685,697 to Arenberg et al., incorporated by reference herein, describes a drug delivery unit for controlled delivery of a therapeutic agent to an internal cavity of the ear, particularly to the inner ear, that includes carrier media material containing one or more therapeutic agents therein. The carrier media material is designed to release the therapeutic agents in a controlled manner over time. The drug delivery unit is shaped and sized for placement of at least a portion thereof in the round window niche of a patient.

Alternatively, body fluid is caused to circulate through a drug-containing reservoir via a recirculating system having two tubes—one for inflow and one for outflow between reservoir and patient. For example, U.S. Pat. No. 5,643,207 to Rise, incorporated by reference herein, describes recirculating body fluid through a drug delivery device for drug delivery to the brain. As another example, U.S. Pat. No. 6,561,997 to Weitzel et al discloses a circuit for extracorporeal treatment of a body fluid.

As another example, one known perfusion technology involves a cochlear implant electrode modified to allow intracochlear drug delivery. In conventional use, the electrode is inserted into the cochlea and used to provide stimulation to the auditory nerve of severely to profoundly hearing impaired individuals. The electrode employed for the drug delivery application, however, contains a removable stylet used for positioning the electrode during insertion. With the stylet removed, the lumen that remains provides the path for drug delivery. The lumen is connected to an osmotic or mechanical pump via a connector and short length of perfusion tubing.

Notably, existing drug delivery technology is typically not appropriate for long-term programmable infusion into the inner ear. The existing approaches for drug delivery devices include external and implanted infusers, osmotic pumps, and erodible polymer-drug systems. These systems range from passive devices, which have a low level of predictability in their dispense rates, to electronically-controlled rate dispensers and finally to fully programmable infusers. Device volumes range from pill size (e.g., those available from Oculex Pharmaceuticals) to over ten cubic inches, generally depending on their maximum dispense volume and sophistication of control. Though small in volume, erodible polymer and porous membrane systems (e.g., iMMED, Inc.) must typically be implemented to deliver a specific compound, or at best, a set of compounds with similar chemistry and transport properties. They are generally short to medium term delivery devices (less than six weeks) with unalterable, non-constant delivery profiles. The existing osmotic pump-based delivery systems (Alzet International, Alza) are similar in terms of device size and lifetime, and they too are capable only of fixed rate delivery. The various available models trade off device size, lifetime, and delivery rate, depending on the application requirements. Infuser technology has primarily been developed by Medtronic (Minneapolis, Minn.). Devices such as the SynchroMed offer sophisticated control and are effective for treatment for some disorders such as chronic pain. However, because they use macro scale conventionally fabricated pumps, these systems are relatively large. They are practical only when implanted in subcutaneous tissue in the torso.

Emerging microsystems present solution to many previously intractable bioengineering challenges. The extension of micorfabrication methods from integrated circuits to many other applications has spawned microelectromechanical systems (MEMS) devices capable of reproducing the functions of conventional sensors and actuators at a fraction of the size and cost. The resulting miniaturization enables complete systems to be integrated into devices small enough to be implanted in close proximity to the organ to be treated. In the case of drug delivery, complex automated dosing regimens can be programmed into the system or even implemented to respond to sensor input of physiological measurements. Several technologies have emerged that may allow controlled release of drug in dried or lyophilized form from discrete compartments.

And so, as described above, developments in cochlear physiology and molecular biology allow for new and innovative ways of treating and preventing sensorineural hearing loss. It is desirable to implement a safe and reliable mechanism for delivering bioactive compounds directly to the inner ear, e.g., a versatile long-term drug delivery system for the treatment of inner ear disorders that will have broad application and the potential for revolutionizing the treatment of hearing loss.

Thus, it is desirable to provide an implantable long-term drug delivery system for treatment of inner ear disorders and prevention of sensorineural hearing loss, specifically, a versatile device that is capable of delivering multiple simple and complex molecules over long periods of time, with capability to control and regulate the sequence and rate of delivery. Such a device can be useful for treatment of idiopathic and inflammatory conditions affecting the inner ear, including autoimmune inner ear disease, cisplatinum induced ototoxicity, and possible Meniere's disease. In addition, a wide spectrum of other degenerative inner ear disorders may be amenable to treatment with such a device, including idiopathic, genetically-based, and age-related progressive sensorineural hearing losses.

SUMMARY OF THE INVENTION

One or more implementations of the invention may provide one or more of the following features. A drug may be infused directly into the human cochlea. Transport of human perilymph, to and from a drug delivery device, may be provided, e.g., for the purpose of transporting therapeutic compounds to the inner ear. Recirculating fluid may be used to fill depleted volume within the device as a drug is dispensed.

One important feature of the invention is enabling recirculating drug delivery using a cannula interface to an internal cavity of a patient, such as, for example, cochlea. For example, in one embodiment of the invention a reciprocating infusion technique can be used to allow recirculation via a single cannula into a body cavity. Also, among other benefits, one of the key features of the invention is providing a device capable of reducing net infusion rates without having to reduce the flow rate delivered by the pump. This is particularly important when no pump is capable of delivering small enough flow rates as required by a physiological limit. Various embodiments of the invention enable recirculation and control of very low flow rates (e.g., less than 1 microliter/minute) as required in the confined volume of the inner ear and other locations.

In general, in one aspect, the invention features an implantable drug delivery apparatus for delivering a drug into a bodily fluid in a body cavity of a patient over a period of time. The apparatus includes a hollow member that defines at least one lumen for facilitating a unidirectional recirculating flow of a therapeutic fluid through the lumen. The fluid can contain a bodily fluid, such as, for example, perilymph, and a drug. The apparatus also includes a pump, for example a single unidirectional pump, to control the flow rate of the therapeutic fluid through the hollow member, and an interface member in communication with at least one lumen of the hollow member. The device thus allows for the controlled delivery of the therapeutic fluid to a predetermined location in the bodily cavity of the patient, such as, for example, a cochlea of a human ear.

In various embodiments of the invention, the interface member is in fluid communication with the bodily fluid in the bodily cavity thereby allowing for drug delivery directly into the bodily fluid. In some versions of these embodiments, the interface member is configured to allow bodily fluid to be periodically drawn from the patient's bodily cavity as the therapeutic fluid is being delivered thereto, allowing for a constant circulation of bodily fluid through the hollow member. This may be achieved, for example, by manufacturing the hollow member from a closed loop of tubing, such as a double-lumen catheter, which travels from the body cavity to the pump. In another embodiment of the invention, a single-lumen cannula, or other equivalent device, can be used as the interface member to connect the hollow member to the body cavity. By constructing a network of tubing with selected resistance, tubing compliance, pump rates, and other parameters, a wide range of desirable transient and oscillating fluid behavior can be achieved in order to inject fluid into the internal cavity of the patient and withdraw fluid from the internal cavity of the patient. In some embodiments of the invention, the fluid capacitance and fluid resistance of at least one of the hollow member and the interface member are selected to obtain an oscillating flow of the therapeutic fluid through the interface member.

Delivering fluid to the perilymph temporarily alters its net volume and therefore results in a change in perilymph pressure. In one embodiment of the invention, the apparatus can be configured to minimize any potential pressure change within the inner ear throughout infusion of a therapeutic agent. However, it has been discovered that periodic pressure pulses delivered to the inner ear can be therapeutic in the treatment of inner ear disorders, such as Meniere's disease. Therefore, in certain embodiments of the invention the apparatus can be configured to manipulate perilymph pressure within the inner ear. This can be achieved by a number of techniques, including, but not limited to, regulating the gauge pressure at the pump inlet or controllably altering the volume of fluid delivered at any one time.

In order to deliver a drug to the body cavity, the drug can be dissolved in the therapeutic fluid, such as a bodily fluid, within the recirculating flow of the hollow member. Dependent upon the requirements for treatment of a patient, the concentration of drug dissolved in the therapeutic fluid may either be varied or held constant. Storage of additional drug to be dissolved in the therapeutic fluid can be facilitated through the addition of a reservoir member for storing the drug, which can include one or more chamber, which is connected to the hollow chamber recirculating the therapeutic fluid through the apparatus. Further control of the drug infusion process can be achieved by adding additional chambers to the reservoir, allowing for more controllable mixing of the drug and therapeutic fluid, and/or the mixing of additional drugs to the therapeutic fluid.

To facilitate the recirculation of the therapeutic fluid through the hollow member a pump can be included within the apparatus. In one embodiment of the invention this pump may be a microelectromechanical (MEMS) microfluidic pump. The pump can be operated at a predetermined frequency, which can be either substantially constant or modulated depending upon the requirements of the system. In a particular embodiment, a flow rate of less than about one microliter per minute.

In various embodiments, control of the flow pattern of the therapeutic fluid through the hollow member is implemented through the use of a control system in electric communication with the pump. Performance parameters regarding the flow pattern of the therapeutic fluid can also be detected by the addition of sensors to the apparatus. The information from these sensors can then be transmitted to a remote device through the use of receiving and transmitting electronics in both the remote device and the apparatus. This configuration can also allow electric signals to be sent from the remote device to the apparatus. The addition of a memory element to the control system for the pump can also be advantageous for such purposes as monitoring the performance of the device and storing control information. In one embodiment, a sensor can be used to detect and, optionally, control flow pattern parameters of the therapeutic fluid.

In various embodiments, the apparatus includes a regulating system for maintaining an optimal drug delivery rate, the regulating system being in communication with at least one the pump and the reservoir. For example, the regulating system may include a sensor for periodically measuring concentration of drug in the therapeutic fluid and/or the bodily fluid and transmitting the measured value of the concentration to the regulating system. In some embodiments, a biosensor could detect a level of a particular molecule of the drug and thereby automatically determine the quantity of drug to release from the reservoir. Also a sensor could measure the concentration of drug in the bodily fluid, such as perilymph, and provide feedback to regulate the drug release rate.

In a particular embodiment of the invention, the apparatus is configured to allow for the long term, for example greater than one year, delivery of a therapeutic fluid to the inner ear of a human. In this embodiment, at least part of the apparatus can be shaped and dimensioned to fit within the mastoid cavity of a human patient. In one version of this embodiment, the interface member to be in fluid communication with a cochlea of the ear. It will therefore be possible, in this and other embodiments, to use human perilymph as the bodily fluid.

In a specific exemplary embodiment, the invention features an implanted apparatus that fits within the mastoid cavity of humans. The apparatus contains an externally-programmable pump to recirculate perilymph, an intracochlear catheter inserted into the scala tympani through a cochleostomy having a cannula in communication with a body fluid of the patient, a mixing chamber with externally programmable delivery of concentrated bioactive compounds, and sensors for detecting and transmitting flow and pressure information. The ultra-miniaturized apparatus is a complete, long-term (one year and greater) delivery system, containing therapeutic compound, dispensing mechanism, control electronics, and power supply.

Alternatively, the apparatus according to the invention can be implemented to deliver drugs to a bodily cavity, such as the cochlea of a human ear, without the need for a recirculating fluid flow within the hollow member connecting the pump to the interface member. Generally, in another aspect, the invention features an implantable drug delivery apparatus for delivering a drug into a bodily fluid in a bodily cavity of a patient over a period of time, which includes a hollow member defining at least one lumen for facilitating a flow of a therapeutic fluid therethrough, the therapeutic fluid containing a first volume of the bodily fluid, such as, for example, perilymph, and the drug contained therein; a pump for controlling a flow rate of the therapeutic fluid through the hollow member; and an interface member in fluid communication with the at least one lumen of the hollow member and the bodily fluid in the bodily cavity, such as, for example, a human cochlea, for delivering at least a portion of the therapeutic fluid into the bodily fluid in a predetermined location in the bodily cavity. In various embodiments of the invention the at least one of the pump and the hollow member is shaped and dimensioned to fit within a mastoid cavity of a human.

In general, in yet another aspect, the invention features a method for delivering a drug into a bodily fluid in a bodily cavity of a patient over a period of time, which includes the steps of drawing a first volume of the bodily fluid from the patient's bodily cavity; mixing the drug with the bodily fluid thereby obtaining a therapeutic fluid; and releasing a first volume of the therapeutic fluid into the bodily cavity.

In various embodiments, the method also includes the step of providing a hollow member defining at least one lumen in communication with the bodily cavity, such as, for example, human cochlea and causing a unidirectional flow of the bodily fluid through the hollow member. The method may further include the steps of controllably recirculating the therapeutic fluid through the hollow member, altering concentration of the drug in the therapeutic fluid during recirculation thereof through the hollow member, and drawing a second volume of the bodily fluid from the bodily cavity. In one example embodiment of the invention, the flow properties of the bodily fluid through the apparatus can depend upon the capacitance and resistance of the hollow member and interface member. Careful selection of the capacitance and resistance can provide an oscillating flow through a single interface member.

In some embodiments, the flow rate of the therapeutic fluid during recirculation through the hollow member is substantially constant. The therapeutic fluid may include a solution of the drug in the bodily fluid, for example, human perilymph.

In a particular embodiment, the method includes controllably altering fluid pressure within the human cochlea, for example, increasing fluid pressure within the cochlea by controllably altering the first volume of therapeutic fluid.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 7 is a table of performance data for exemplary embodiments of the invention.

DETAILED DESCRIPTION

Figure 1:
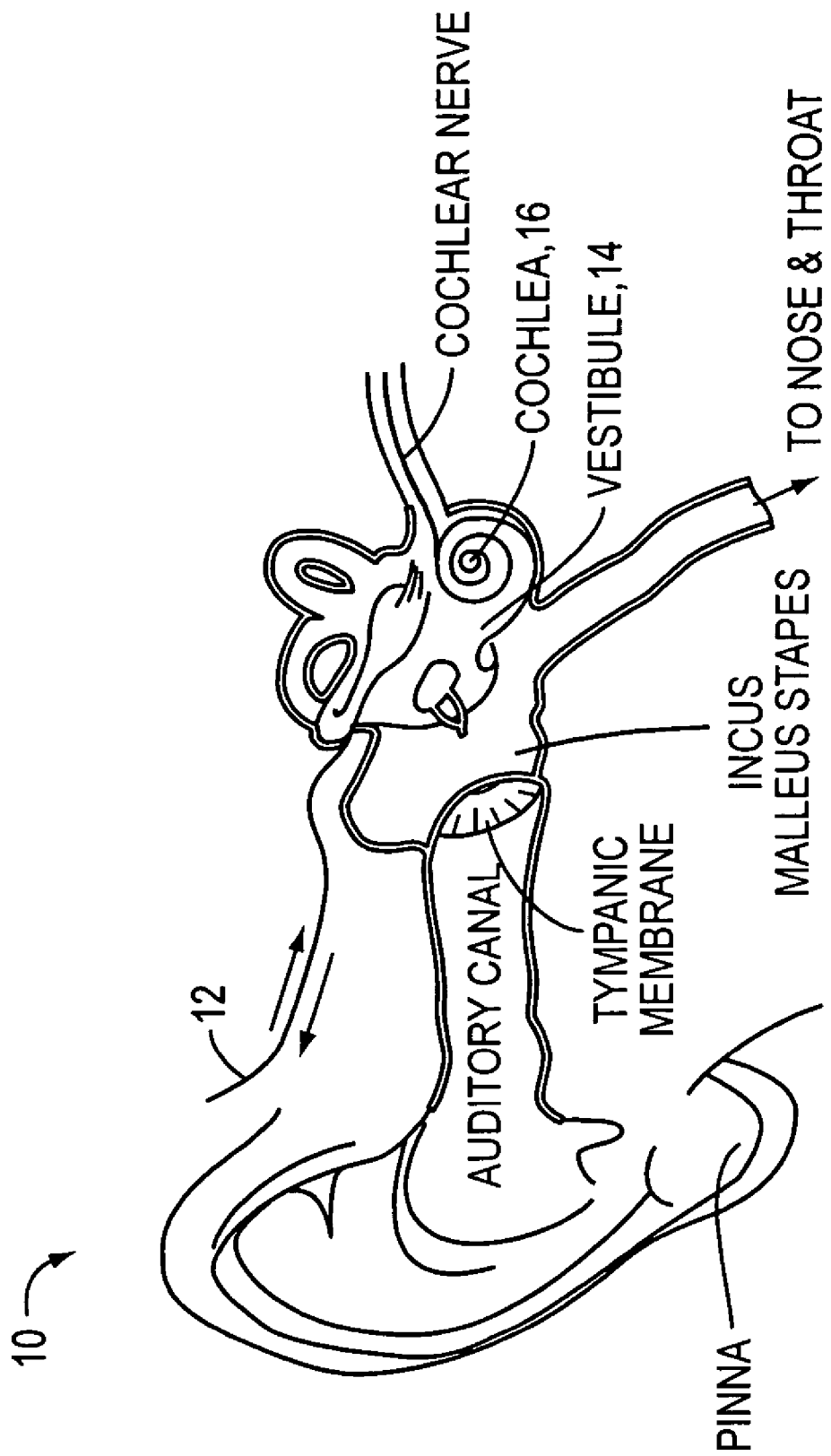
FIG. 1 depicts a sketch of a human inner ear with an implanted drug delivery system, in accordance with various embodiments of the invention.

As discussed above, conventional drug infusers utilize macroscale machined components to pump liquid drugs from a reservoir. The invention provides for replacing these components with a synthesis of micropumps and MEMS solutions for drug storage and release, which will result in smaller devices with greater functionality. This will enable the opening of the inner ear and other previously inaccessible locations in the body for new direct treatment, without the side effects of systemic delivery.

Microfluidics and microelectromechanical systems (MEMS) capability can be used for drug delivery applications, to allow or provide a controlled rate, low drug volume, and/or liquid formulation) e.g. for an implantable inner ear delivery system). In an example embodiment, a fluidic system having a closed loop microfluidic flow controller can be used with animal test apparatus. In one embodiment of the current invention, an implanted recirculating delivery system can be used in therapy for hearing loss and Meniere's disease. An example delivery system may employ a number of commercially available pumps, such as, but not limited to, a Wilson Greatbatch insulin pump or MEMS pump, such as those available from Debiotech.

In some embodiments, the micromechanical device for intracochlear drug delivery discloses utilizing a surgical approach that is similar to cochlear implantation, but minimizes cochlear insult. The implementation concept includes a double lumen intracochlear catheter inserted into scala tympani through a cochleostomy adjacent to the round window. In its implanted position, it is similar to cochlear implants that also traverse the tympanomastoid cavity with electrodes positioned within the cochlea, except that the depth of insertion is much less.

In accordance with the invention, drug delivery to the ear relies on a method in which a recirculating stream of fluid from the patient is passed through a device and is infused remotely rather than within the tissue, which enables recirculation and control of very low flow rates (e.g., less than 1 microliter/minute) as required in the confined volume of the inner eat. A specific application with respect to inner ear diseases provides for direct infusion of the cochlea through a catheter, using an implanted device to programmably and continually deliver drugs through the catheter.

The recirculating fluid permits the reservoir to contain a highly concentrated solution, and therefore can potentially produce a device that operates for years without refilling. This greatly reduces the risk of microbial contamination during refill. Another benefit is using a vehicle that is inherently biochemically compatible. In addition, the perilymph may circulate through the catheter at a rate that is independent of the drug delivery rate. Thus these parameters can be optimized separately. It is likely that frequent circulation of the perilymph will maintain patency in the catheter, whereas a slow one-way drug infusion would occlude. Finally, because there is controlled supply of liquid solvent, it is not necessary to use a liquid drug reservoir. The drug storage could take any number of forms, such as microchip arrays, bio-erodible polymers, or even hybrid combinations of these drug delivery methods.

In a specific exemplary embodiment, a microfluidic pump recirculates human perilymph, which is withdrawn and returned to the inner ear through a catheter, implanted through the round window membrane or adjacent tissue. Drugs are injected into this recirculating stream from one or more reservoirs by one or more microvalves and/or one or more other drug release methods.

As used herein, the term "drug" is understood to mean any natural or synthetic, organic or inorganic, physiologically or pharmacologically active substance capable of producing a localized or systemic prophylactic and/or therapeutic effect when administered to an animal. A drug includes (i) any active drug, (ii) any drug precursor or pro-drug that may be metabolized within the animal to produce an active drug, (iii) combinations of drugs, (iv) combinations of drug precursors, (v) combinations of a drug with a drug precursor, and (vi) any of the foregoing in combination with a pharmaceutically acceptable carrier, excipient, or formulating agent.

The drug or drugs of interest may be stored in the apparatus either in pure form or as a formulation, for example, in combination with a pharmaceutically acceptable carrier or encapsulated within a release system. A release system can include a matrix of a biodegradable material or a material which releases incorporated drug by diffusion. The drugs can be homogeneously or heterogeneously distributed within the release system. A variety of release systems may be useful in the practice of the invention, however, the choice of the appropriate system will depend upon rate of drug release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar. Release systems may be natural or synthetic. However, synthetic release systems are preferred because generally they are more reliable, more reproducible and produce more defined release profiles. The release system material can be selected so that drugs having different molecular weights are released from a particular cavity by diffusion through or degradation of the material. Biodegradable polymers, bio-erodible hydrogels, and protein delivery systems currently are preferred for drug release via diffusion or degradation.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Preferably, the storage capabilities of the apparatus are such that it holds sufficient amount of the drug to provide a continuous delivery over the extended delivery period, e.g., several weeks, months, or even longer. The storage volume needed thus depends on characteristics such as drug solubility, drug delivery rate, period of delivery, drug's half life, etc. Once implanted, the device continuously delivers the drug for prolonged period of time until replenishment.

In various embodiments of the invention, communication with a remote device external to the patient's body and capable of controlling of the infusion rate allows for modification of the therapy in response to a patient's symptoms and reactions. This feature may include control of the recirculation rate to allow different dosage schemes, such as, but not be limited to, either steady low concentrations or intermittent high concentrations of drugs. Variation of the dosage based on the time of day can also be desirable.

In addition to performance features, a number of safety features may also be included in embodiments of the invention. Example features may include, but not be limited to, automatic shutoff control if pressure or flow sensors give abnormal readings, self-diagnostic routines which may run automatically or upon prompting from an external controller. In one embodiment of the invention, telemetry can enable a physician to interrogate settings, identify low battery or other alarm signals, and obtain device identification or serial number. A clinician may communicate with the device by means of a hand-held module connected to a personal computer, or through another analogous communication device.

The ability to communicate with implanted electronic devices has been well established over the last 25 years (e.g. with pacemaker systems). As such, communicating with and controlling the drug delivery device does not pose a major problem. Nonetheless, the communication subsystem must guarantee reliable and robust operation, since minimal service and adjustment is possible after installation.

As a result of its ubiquitous application, communication via the wireless RF technique offers one approach for remote communication. In addition to enabling a small low-cost device, the RF technique also provides a convenient means by which the battery energy may be replenished. Although recent studies have concentrated on frequencies above a few hundred megahertz, these studies have been motivated by the need to distribute real-time image information. The bandwidth requirements for the drug delivery device are much more modest. A frequency of 10 MHz helps minimize attenuation due to skin effect, while at the same time allows use of a small, low profile antenna.

Several additional physical means are also available for coupling communication signals from the implanted device to an external interrogator or programmer. In one embodiment of the invention, mechanical (acoustic) waves may provide a communication mechanism. The acoustic technique is enabled by the recent availability of miniature transducers fabricated with MEMS technology. Further embodiments may include, but not be limited to, the use of optical means or direct volume conduction to communicate with an implanted device.

One embodiment of the current invention can be seen in the illustration of FIG. 1. Referring to FIG. 1, an implanted recirculating delivery system directs fluid to and from the cochlea of a human ear 10. A double lumen catheter 12 is implanted a body and is in communication with the vestibule 14 and cochlea 16 of the inner ear. This arrangement allows a fluid to recirculate between the cochlea 16 and an external or internally planted pump (not shown).

Figure 2B:
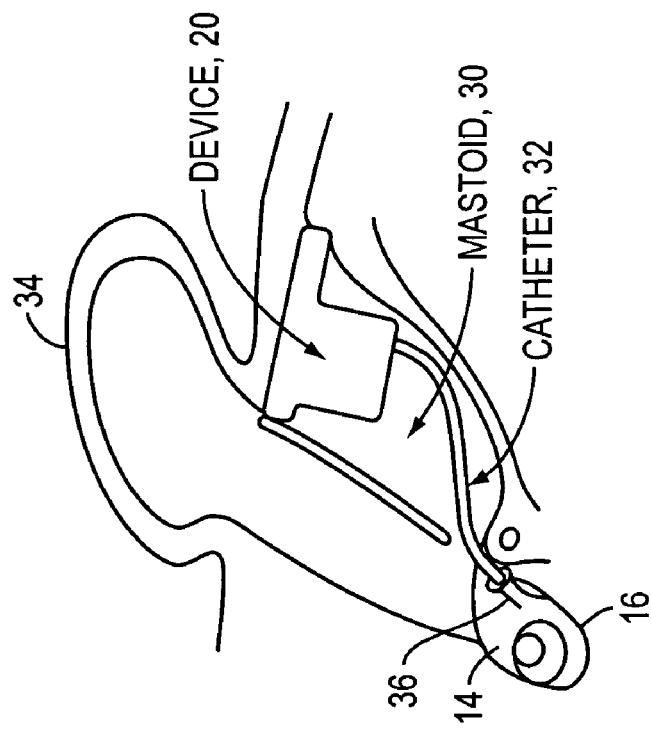
FIG. 2B depicts a sketch of a exemplary drug delivery apparatus implanted in the mastoid cavity of a human ear.
Figure 2A:
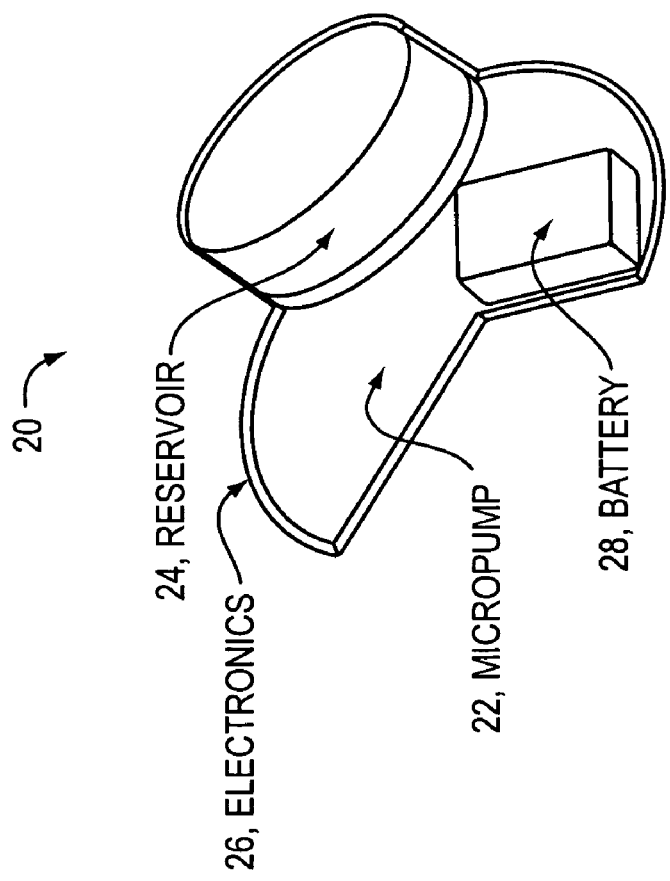
FIG. 2A is a schematic view of an exemplary drug delivery apparatus that includes a pump, reservoir, electronics and battery system, in accordance with one embodiment of the invention.

An exemplary embodiment of the invention with an electronic device imbedded within the mastoid cavity of a human ear can be seen in FIGS. 2A and 2B. In FIG. 2A, a device 20 includes a micropump 22 connected to a reservoir 24. The flow rate produced by the pump 22, and the rate at which a drug is released by the reservoir 24, can be controlled by control system 26 integrated within the device 20. Power can be supplied to the system through a battery 28, which can also be imbedded in the device 20. Alternative embodiments of the device 20 may incorporate additional features, such as but not limited to further reservoirs or additional electronic features, but can also be simplified by removing attachments shown herein, such as the reservoir 24. For example, drug storage within the device can be achieved through a number of methods such as, but not limited to, the use of a fluid chamber with a valve connection, the addition of bio-erodible polymers, the addition of multiple reservoirs 24 containing multiple drugs, and the addition of storage devices capable of delivering solid or powdered drug formulations.

The device 20 illustrated in FIG. 2A can be seen implanted within the mastoid cavity 30 of a human ear, in accordance with one embodiment of the invention. In this embodiment, the device 20, incorporating the micropump 22, reservoir 24, control system 26, and battery 28, is implanted behind the pinna 34 of a human ear, within the mastoid cavity 30. The device is connected to a double-lumen catheter 32, which connects to an interface member, in this case a cannula 36, which is implanted into the vestibule 14 of a human ear, thus allowing fluid communication with a cochlea 16.

Various configurations of the device allow a drug, or drugs, to be mixed with the therapeutic fluid recirculating within the double-lumen catheter 32. Depending upon the requirements of the system, the infusion of a drug into the therapeutic fluid can be constant or modulated. The flow rate of the therapeutic fluid within the system can also be controlled through the control of the micropump 22, which can either be held at a substantially constant frequency or modulated. The control system 26 in the device can control the flow and infusion rate, and also provides the possibility of monitoring the performance of the device 20, send information regarding the flow parameters to a remote device, and receive information from a remote device. In various embodiments, the device includes a regulating system that is used to determine optimal drug delivery rates. In some embodiments, the regulating system is part of the control system 26. In one particular embodiment, a biosensor of the regulating system detects a level of a particular molecule of the drug and thereby enables the regulating system to automatically determine the quantity of the drug to release from the reservoir. Also, a sensor of the regulating system could also measure the concentration of drug in the perilymph and provide feedback to regulate the drug release rate from the reservoir or increase the flow rate by the pump.

Figure 3A:
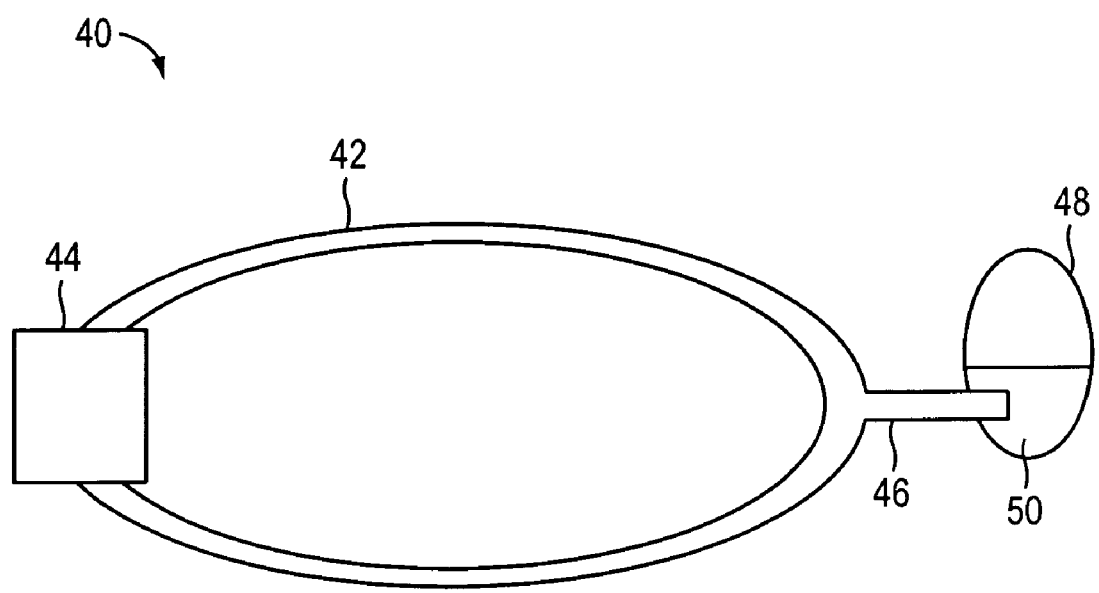
FIG. 3A is a schematic view of a recirculating drug delivery apparatus in accordance with some embodiments of the invention.
Figure 3B:
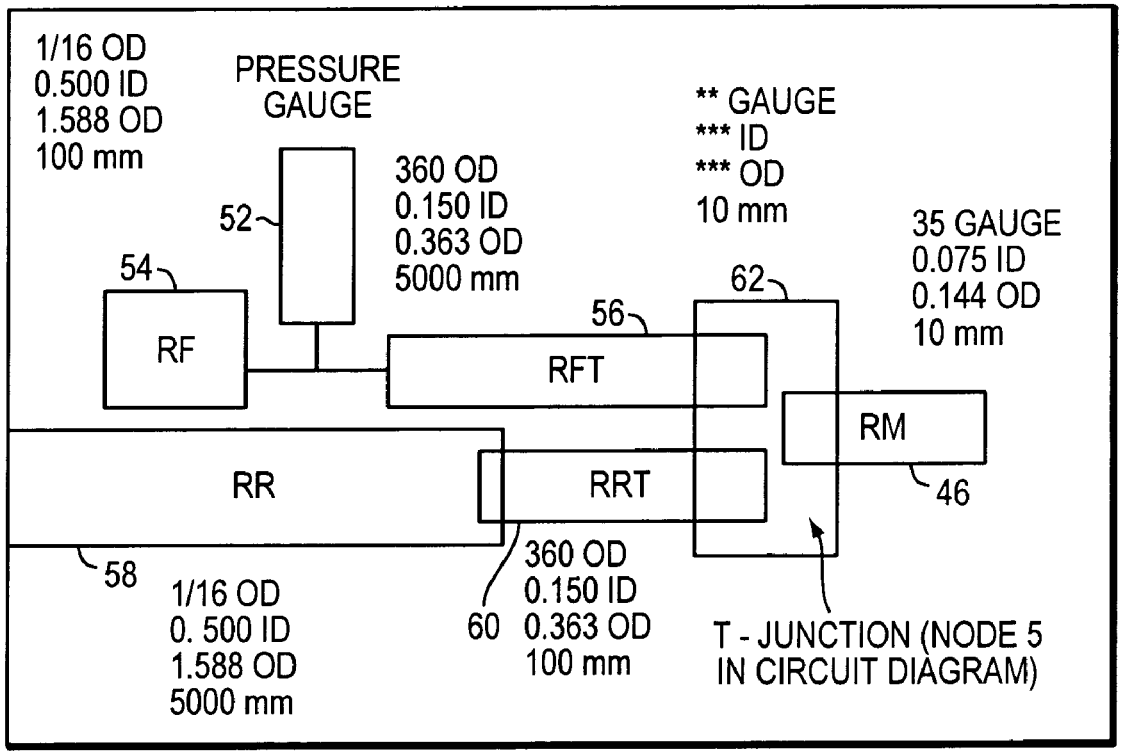
FIG. 3B-3C depict schematic diagrams for the drug delivery apparatus of FIG. 1A.
Figure 3C:
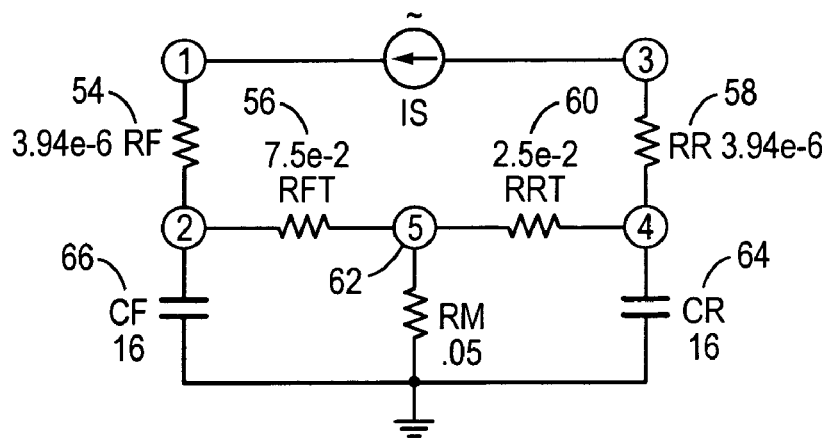

A schematic for the basic fluid circuit is shown in FIGS. 3A to 3C. Referring to FIG. 3A, in one embodiment, a drug delivery system 40 has been designed without a distinct supply reservoir. As a result, it recirculates a constant net volume of fluid through a loop of tubing 42 driven by a micropump 44. The recirculating stream communicates through a lumen of a cannula 46 with the cochlea 48, depicted here for simplicity as an open reservoir containing fluid 50. Delivery occurs through transport outside of the system: fluid expelled during the first half pump cycle equilibrates with the fluid in the outside reservoir, either through diffusion or mixing, thus the fluid drawn in during the next half cycle is less concentrated and net delivery occurs, albeit decreasing over time. In various embodiments, design of the system 40 enhances mixing by achieving an oscillatory flow of sufficient amplitude to completely expel the fluid contained in the cannula 46 during a cycle. Otherwise "fresh" compound would not be delivered each cycle, in effect, mixing would largely be dominated by diffusion in the small volume of the cannula 46.

FIGS. 3B and 3C, respectively, depict a plumbing diagram for the recirculating fluidic delivery system and its equivalent lumped-element electric circuit schematic. FIG. 3B depicts a schematic diagram for the system 40, with the addition of a pressure gauge 52. The pressure gauge 52 is connected to the feed leg of the hollow member, which comprises two sections of differing diameter 54 and 56. The return leg of the hollow member comprises the two sections of differing diameter 58 and 60. The hollow member connects through a T-junction 62 to the cannula 46. FIG. 3C depicts a circuit representation of the system of FIG. 3B. Here, the resistance of the sections of each hollow member section 54, 56, 58, and 60 are shown, along with the resistance within the cannula 46 and the capacitance in the feed and return legs 64 and 66.

By careful selection of the geometric properties of the cannula 46 and hollow member sections 54, 56, 58, and 60, the flow pattern properties within the system, and the resulting drug delivery rates to the cochlea 48, can be controlled. In a particular embodiment of the invention, selection of the systems geometric properties and the operation properties of the micropump 44 can produce a reciprocating flow within the system. In this configuration, the fluid capacitance and fluid resistance of within the delivery system can be selected and, optionally, controllably altered, to provide an oscillating flow through a single cannula 46. This flow regime can have a number of important benefits, such as, but not limited to, improving mixing of the drug and perilymph within the delivery system and cochlea 48, carefully controlling the rate of drug delivery to the cochlea 48, and helping to avoid occlusion within the tubing. This configuration also allows for a transport of fluid into and out of the cochlea 48 using only a single interface member.

In some embodiments, the micropump driving the fluid is a reciprocating solenoid pump (such as a Wilson Greatbatch WGL 05) with a 0.5 uL fixed stroke volume operating up to 20 psi. The transition time of the pump stroke is preferably much smaller than the pump cycle time, which is 0.33 sec minimum (3 Hz maximum pumping frequency). The nominal feed and return tubing between the pump and T-junction are each approximately 50 cm long with negligible resistance, having an I.D. of 1.0 mm. These tubes may function as the primary source of compliance (CF and CR described below) and could vary in material from silicone (modulus ~10 MPa) to PEEK (modulus 1 GPa). The T-junction capillaries are rigid (fused silica). The tubes represented by RFT and RRT should have I.D. less than 250 um (not necessarily equal) and length of at least 10 mm. The cannula 46 is assumed fixed, because of surgical constraints, with I.D. 75 um and length 20 mm.

To satisfy the above condition, one half of a flow cycle must generate a fluid flow volume of at least that of the mixing tube volume.

$$V_M = \frac{\pi}{4} \cdot D_{IM}^2 \cdot L_M = 0.088 \text{ uL} \qquad \text{(Formula 1)}$$

Given the circuit configuration, it is difficult to achieve this without some capacitance in the system. Specifically, with the fluidic capacitors shown in FIG. 3C removed, there is no loop that includes the mixing output leg RM through which fluid can flow. Equivalently, there is no storage capability in the pump loop which allows fluid to be stored in such a way that the flow rates in the T-feed and T-return sections can be unequal at the same instant in time, which is the only condition under which fluid may flow in the cannula.

In one embodiment of the fluidic delivery system described in FIGS. 3A to 3C, the micropump can be configured to operate continuously at a predetermined frequency. In a second embodiment, the micropump input can be modulated so that it periodically turns on and off at some frequency much lower than the pump cycle frequency, and also more slowly than the largest system time constant.

In order to analyze the system described in FIGS. 3A to 3C, a number of system parameters must be calculated for the component geometry and properties, and a number of simplifying approximations must be made. For example, the pump pulse time is estimated to be of the order of milliseconds.

Also, the resistance to fluid flow of a tube with circular and constant cross section can be given by;

$$R = \frac{128 \cdot \eta \cdot L}{\pi \cdot D_I^4} \quad \text{(Formula 2)}$$

where $\eta$ is the dynamic viscosity, L the tube length and $D_I$ the inner diameter.

For an expandable piece of tubing, the capacity to store fluid can be approximated by;

$$C \equiv \frac{dV}{dP} = \frac{\pi \cdot L \cdot D_I^3}{2 \cdot E_Y \cdot (D_O - D_I)} \quad \text{(Formula 3)}$$

where $E_Y$ is the elastic modulus, $D_O$ is the outer diameter, and $D_I$ again refers to the tube inner diameter. Alternatively, to use the compressibility of a length of air bubble in a portion of tubing, the capacitance can be described approximately by;

$$C = \frac{L_0 \cdot \pi \cdot D_I^2 \cdot P_0}{4 \cdot P^2} \quad \text{(Formula 4)}$$

where $L_0$ is the length of the bubble when at pressure $P_0$, and P is the bubble pressure. It should be noted that this expression describes a non-linear element (i.e. it is dependent on the pressure). For analysis, the average pressure of the bubble (i.e. $P = P_{avg}$) gives reasonably accurate estimates of the bubble capacity as long as the average is large compared to its maximum deviation from that average.

Laplace domain analysis of the circuit in FIGS. 3A to 3C yields the transfer function;

$$\frac{I_0}{I_S} = \frac{-A_0 \cdot \omega_n^2 \cdot s}{(s^2 + 2 \cdot \zeta \cdot \omega_n \cdot s + \omega_n^2)} = \frac{-A_0 \cdot \omega_n^2 \cdot s}{(s + \omega_H) \cdot (s + \omega_L)} \quad \text{(Formula 5)}$$

where $I_0$ is the fluid flow through the output tube, $I_S$ is the source flow, and the system gain, undamped natural frequency, damping ratio, and high and low frequency poles are given respectively by;

$$A_0 = R_{FT} \cdot C_F - R_{RT} \cdot C_R \quad \text{(Formula 6)}$$

$$\omega_n = \lfloor C_F \cdot C_R \cdot (R_{FT} \cdot R_{RT} + R_{FT} \cdot R_M + R_M \cdot R_{RT}) \rfloor^{-\frac{1}{2}} \quad \text{(Formula 7)}$$

$$\zeta = \frac{\omega_n \cdot (R_M \cdot C_R + R_{FT} \cdot C_F + R_{RT} \cdot C_R + R_M \cdot C_F)}{2} \quad \text{(Formula 8)}$$

$$\omega_H = \left( \zeta + \sqrt{\zeta^2 - 1} \right) \cdot \omega_n \quad \text{(Formula 9)}$$

$$\omega_L = \left( \zeta - \sqrt{\zeta^2 - 1} \right) \cdot \omega_n$$

It can be shown, by taking partial derivates of Formula (8) with respect to the various circuit elements, that the damping ratio $\xi$ for this system is always greater than or equal to one, and in fact is only equal to one in two trivial non-useful scenarios, and thus the system never has an under-damped, decaying-oscillation response to an impulse or unit step input.

Figures 4A, 4B:
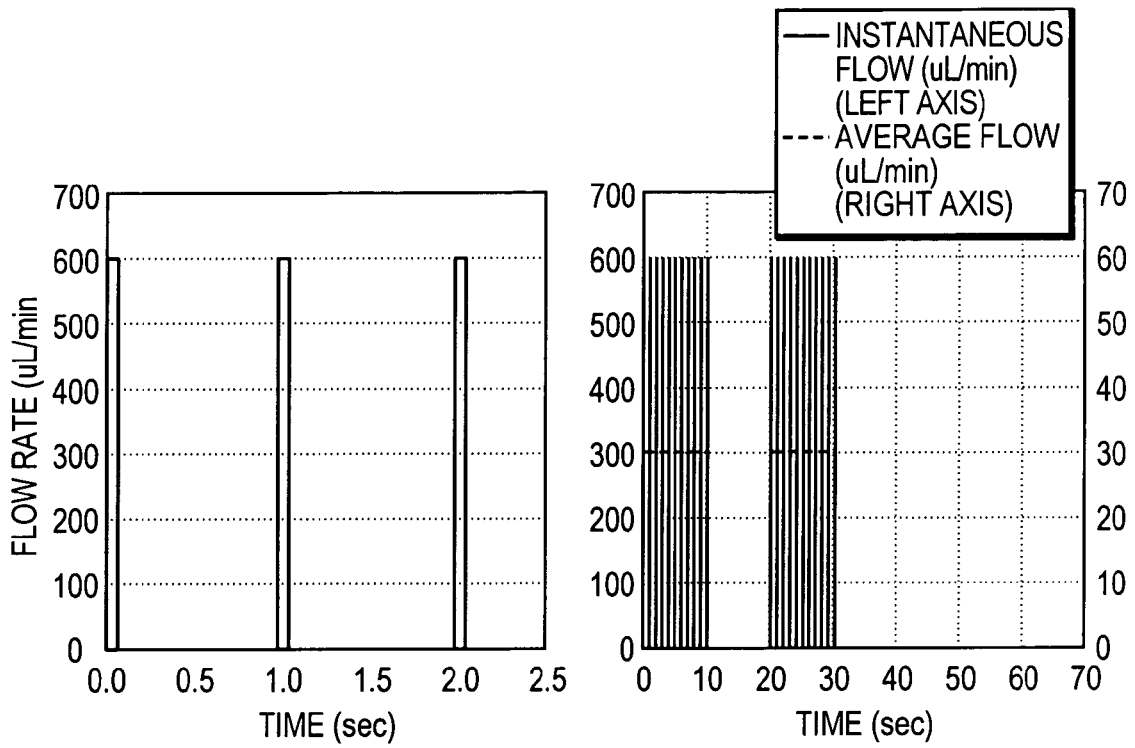
FIG. 4A is a plot of an example pump flow output for a pump operating at a constant frequency, in accordance with one embodiment of the invention.
FIG. 4B is a plot of an example flow rate for a pump which is periodically turned on and off at a frequency lower than the pump cycle frequency, in accordance with one embodiment of the invention.

FIG. 4A depicts a qualitative plot of the pump flow output for the configuration wherein the micropump is configured to operate continuously at a predetermined frequency. Here, the cycle frequency is 1 Hz and the pulse time is 0.05 sec. In this operating mode, the system design time constants are large compared to the pulse time but small compared to the pump cycle period. As a result, the input can be modeled as an impulse function. A single pulse of the pump would be expected to generate a transient flow event such that the total volume exchange during that event exceeded that given by the above stated Formula (1).

The volume impulse response is given by;

$$V_{imp} = \frac{V_{stroke} A_0 \cdot \omega_n}{2 \cdot \sqrt{\zeta^2 - 1}} \cdot (\exp(-\omega_H \cdot t) - \exp(-\omega_L \cdot t)) \quad \text{(Formula 10)}$$

where, as mentioned above, it is assumed that the stroke volume is delivered in a time interval small compared to all system time constants. This results in a maximum volume exchange of $$V_{cycl} = \frac{V_{stroke} A_0 \cdot \omega_n}{2 \cdot \sqrt{\zeta^2 - 1}} \cdot \left[ \left(\frac{\omega_H}{\omega_L}\right)^{\frac{\omega_H}{\omega_L - \omega_H}} - \left(\frac{\omega_H}{\omega_L}\right)^{\frac{\omega_L}{\omega_L - \omega_H}} \right] \quad \text{(Formula 11)}$$

The maximum flow rate produced within the mixer tube, which occurs at t=0, is given by;

$$I_{imp\_max} = \frac{-V_{stroke} A_0 \cdot \omega_n \cdot (\omega_H - \omega_L)}{2 \cdot \sqrt{\zeta^2 - 1}} \quad \text{(Formula 12)}$$

Control of the performance characteristics of the device can be achieved by careful selection of the parameters of the device. Design inputs, such as, but not limited to, the inner and outer diameters of the tubing in the double-lumen catheter and the cannula interfacing with the body cavity, the pump frequency and the stroke volume may be set to produce the performance characteristics required for a given design.

Figures 5A, 5B:
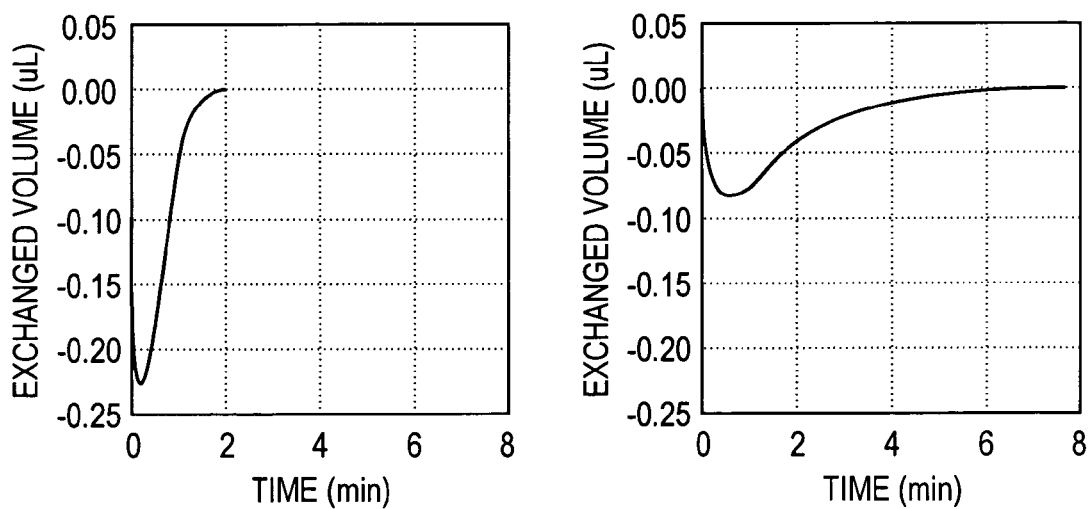
FIG. 5A is a plot of an example output flow for one example delivery system design with a pump operating at a constant frequency, in accordance with one embodiment of the invention.
FIG. 5B is a plot of a second example output flow for one example delivery system design with a pump operating at a constant frequency, in accordance with one embodiment of the invention.

Example data for two sets of design inputs, specifically for an example high flow and low flow configuration, can be seen in FIGS. 5A and 5B. The relevant input data and calculations can be found in the spreadsheet of FIG. 7. In each case, the stroke volume was set to 0.5 uL. It can be seen from the results that the high flow configuration exchanges about three times the mixer tube volume, while the low flow configuration exchanges a volume approximately equal to that of the mixer tube. It should be noted that the flow rates vary substantially with time. For example, in the high flow configuration, the system draws 0.22 uL into the system in approximately 10 sec, but takes approximately 1.5 min to fully expel it.

By setting the device to operate continuously at a predetermined frequency, a relatively small exchange volume (only several times that of the mixer tube volume) and flow rates is possible. Also, the pump frequency should be slow compared to $\omega_L$. The calculations used in the spreadsheet of FIG. 7 calculates a pump frequency which is 3 times slower than $\omega_L$. This margin can be adjusted depending on the desired pumping characteristics.

In an alternative embodiment of the invention, the micropump input can be modulated so that it periodically turns on and off at a frequency much lower than the pump cycle frequency, and also more slowly than the largest system time constant. In this operating mode, the system time constants are large relative to both the pulse time and the pump cycle period. As a result, the pump effectively looks like a constant current (flow) source rather than a pulse train, as can be seen in FIG. 4B, which depicts a qualitative plot of the pump flow output with respect to time. The resulting flow rate in this configuration is given by;

$$I_{SO} = V_{stroke} \cdot f_p \qquad \text{(Formula 13)}$$

where $V_{stroke}$ is the pump's stroke volume and $f_p$ the pump frequency. In this case, the pump is modeled as a step function current (flow) source, again, assuming it is left "on" longer than the longest system time constant.

The step input in Laplace domain is given by $$I_S = \frac{I_{SO}}{s},$$

so Formula (5) becomes;

$$\frac{I_{us}}{I_{SO}} = \frac{-A_0 \cdot \omega_n^2}{(s^2 + 2 \cdot \zeta \cdot \omega_n \cdot s + \omega_n^2)} \qquad \text{(Formula 14)}$$

and the time domain step response is;

$$I_{us} = \frac{-I_{SO} A_0 \cdot \omega_n}{2 \cdot \sqrt{\zeta^2 - 1}} \cdot (\exp(-\omega_L \cdot t) - \exp(-\omega_H \cdot t)) \qquad \text{(Formula 15)}$$

where $I_{SO}$ is the pump flow rate amplitude. The time dependent response approaches zero for large time, due to the decaying exponentials. Its integral, the fluid volume, is given by;

$$V_{us} = \frac{-I_{SO} \cdot A_0 \cdot \omega_n}{2 \cdot \sqrt{\zeta^2 - 1}} \cdot \qquad \text{(Formula 16)}$$

$$\left( \frac{\exp(-\omega_H \cdot t)}{\omega_H} - \frac{\exp(-\omega_L \cdot t)}{\omega_L} + \frac{2 \cdot \sqrt{\zeta^2 - 1}}{\omega_n} \right)$$

which asymptotically approaches a constant value, given by;

$$V_{cycus} = -I_{SO} \cdot A_0 \qquad \text{(Formula 17)}$$

As in the cases with a continuously operating micropump, the maximum flow rate in this configuration is critical to the design, and is given by;

$$I_{us\_max} = \frac{-I_{SO} A_0 \cdot \omega_n}{2 \cdot \sqrt{\zeta^2 - 1}} \cdot \left[ \left(\frac{\omega_L}{\omega_H}\right)^{\frac{\omega_L}{\omega_H - \omega_L}} - \left(\frac{\omega_L}{\omega_H}\right)^{\frac{\omega_H}{\omega_H - \omega_L}} \right] \qquad \text{(Formula 18)}$$

Figure 6A:
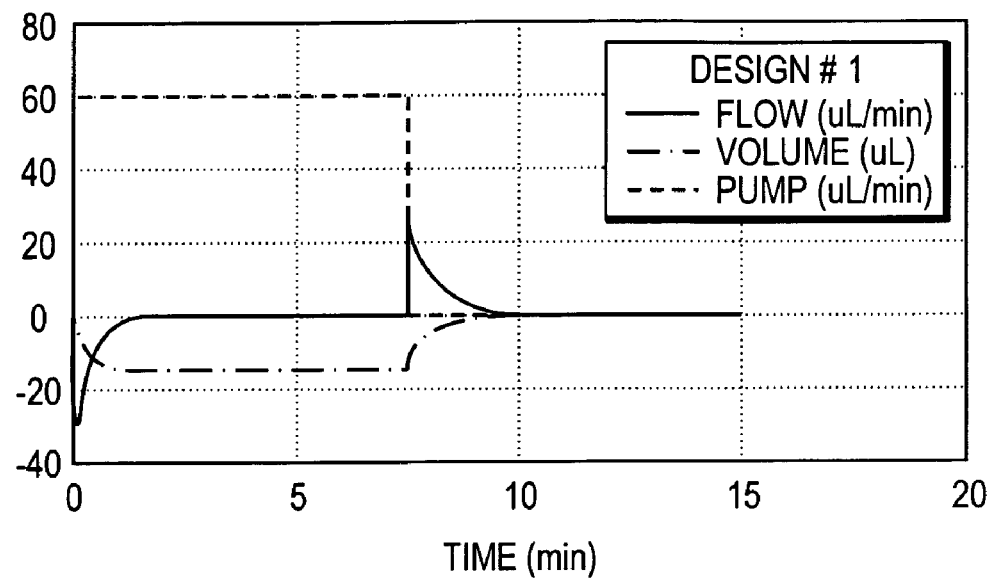
FIG. 6A is a plot of an example output flow for one example delivery system design with a pump which is periodically turned on and off at a frequency lower than the pump cycle frequency, in accordance with one embodiment of the invention.
Figure 6B:
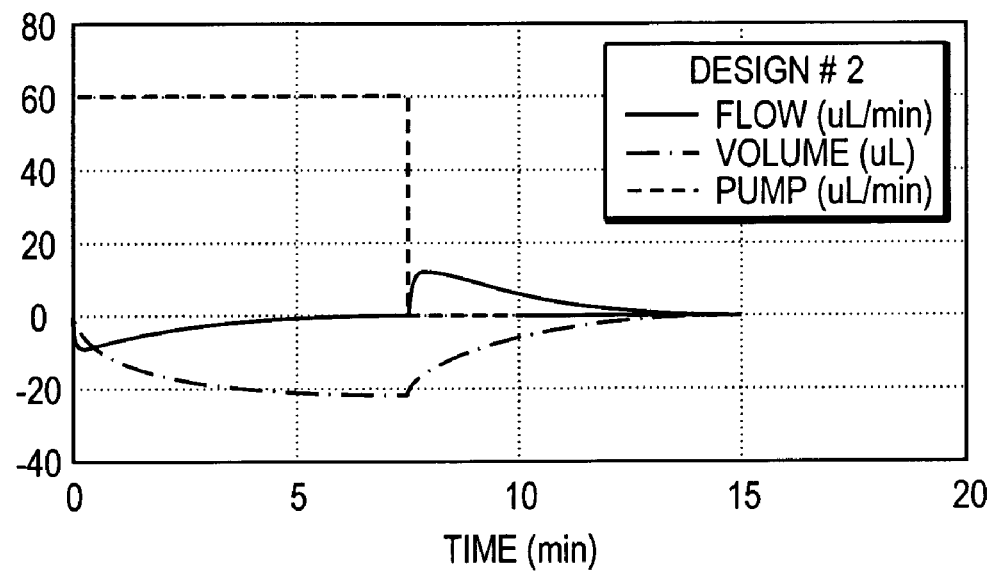
FIG. 6B is a plot of a second example output flow for one example delivery system design with a pump which is periodically turned on and off at a frequency lower than the pump cycle frequency, in accordance with one embodiment of the invention.

Predicted output data for the configuration where the micropump input is modulated can be seen in FIGS. 5A and 5B. Again, data is shown for two sets of design inputs, specifically for an example low flow and high flow configuration. The high flow case, shown in FIG. 6B, clearly generates a larger volume exchange, but because of the larger system time constants, has a lower maximum flow rate than the lower flow configuration. In this case, the larger capacitances more than compensate for the reductions in feed resistances in producing larger time constants and system gain $A_0$. In using the embodiment wherein the micropump input is modulated, it should be noted that the volume exchanges shown will be achieved only if the modulation time is large relative to the slowest time constant.

In choosing system components to optimize performance, it should be noted that the maximum pressure developed at the pump is given by;

$$P_{max} = I_{SO} \cdot (R_{FT} + R_{RT} + R_F + R_R) \qquad \text{(Formula 19)}$$

Thus, it is important to choose component values carefully such that the pump will perform properly. It should be noted that In each of the above example embodiments only the primary feed and return lines were assumed to have sufficient compliance to contribute significantly to the capacitance in the system. The elastic modulus used in the calculations was 11 MPa.

It can be seen that by modulating the micropump input, substantially larger exchange volumes and flow rates are possible than for the examples where the micropump operates continuously at a predetermined frequency. The pump frequency is used to set the average flow rate. The exchange volume and flow rate are directly proportional to this average flow rate and thus the pump frequency.

It should be noted that the equations and example data shown here are only accurate for cases wherein the pump frequency is not comparable to $\omega_L$. Specifically, the error is 10% at $f_p = 2\omega_L$, and will increase as $f_p$ is decreased. Further, the pump on-off modulation frequency should be slow compared to $\omega_L$. The example data is calculated for a pump modulation frequency which is three times slower than $\omega_L$. This margin can be adjusted depending on the desired pumping characteristics.

The invention may be embodied in other specific forms without departing form the spirit or essential characteristics thereof. The foregoing embodiments, therefore, are to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A drug delivery apparatus for delivering a drug into a bodily fluid in a body cavity over a period of time, the apparatus comprising:
    a hollow member defining at least one lumen for facilitating a unidirectional recirculating flow of a therapeutic fluid therethrough,
    a cannula in fluid communication with the hollow member for facilitating bidirectional fluid flow through a lumen of the cannula to and from the bodily cavity; and
    a pump for controlling a flow rate of the therapeutic fluid through the hollow member, thereby alternately delivering fluid from the hollow member to the bodily cavity through the lumen of the cannula and drawing bodily fluid from the bodily cavity into the hollow member through the lumen of the cannula.

2. The apparatus of claim 1 wherein the body cavity is a cochlea of a human ear.

3. The apparatus of claim 1 wherein the bodily fluid comprises human perilymph.

4. The apparatus of claim 1 wherein the hollow member comprises a closed loop of tubing or at least one elongated member defining at least one sealed channel.

5. The apparatus of claim 4 wherein the loop of tubing comprises a double-lumen catheter.

6. The apparatus of claim 1 wherein the fluid capacitance and fluid resistance of at least one of the hollow member and the cannula are selected to obtain a reciprocating flow of the therapeutic fluid through the cannula.

7. The apparatus of claim 1 wherein the drug is dissolved in a first volume of bodily fluid.

8. The apparatus of claim 1 wherein a concentration of the drug in the hollow member varies as fluid reciprocatingly flows through the lumen of the cannula.

9. The apparatus of claim 1, further comprising a reservoir member for storing the drug, the reservoir member defining a first chamber in communication with the at least one lumen of the hollow member.

10. The apparatus of claim 9 wherein the reservoir member defines a second chamber in communication with the first chamber for controllably mixing the drug with the bodily fluid.

11. The apparatus of Claim 9 further comprising a regulating system for maintaining a drug concentration in the hollow member, the regulating system being in communication with at least one of the pump and the reservoir.

12. The apparatus of claim 11 wherein the regulating system comprises a sensor for periodically measuring concentration of drug in the therapeutic fluid and transmitting the measured value of the concentration to the regulating system.

13. The apparatus of claim 11 wherein the regulating system comprises a sensor for periodically measuring concentration of drug in the bodily fluid and transmitting the measured value of the concentration to the regulating system.

14. The apparatus of claim 1 wherein the pump comprises a microelectromechanical microfluidic pump operating at a predetermined frequency.

15. The apparatus of claim 14 wherein the frequency of the pump is substantially constant.

16. The apparatus of claim 14 wherein the frequency of the pump is modulated.

17. The apparatus of claim 1 wherein the pump causes the therapeutic fluid to flow through the hollow member at the flow rate of less than about one microliter per minute.

18. The apparatus of claim 1 further comprising a control system in electric communication with the pump for controlling a flow pattern of the therapeutic fluid through the hollow member.

19. The apparatus of claim 18 wherein the control system comprises a receiver for receiving electric signals from a remote device.

20. The apparatus of claim 18 wherein the control system comprises a transmitter for transmitting electric signals to a remote device.

21. The apparatus of claim 18 wherein the control system comprises a memory element.

22. The apparatus of claim 18 further comprising at least one sensor in communication with the control system for detecting and transmitting data to the control system.

23. The apparatus of claim 22 wherein the data is selected from the group consisting of: at least one flow pattern parameter of the therapeutic fluid, concentration of the drug in the therapeutic fluid, and concentration of the drug in the bodily fluid.

24. The apparatus of claim 1 wherein at least one of the pump and the hollow member is shaped and dimensioned to fit within a mastoid cavity of a human.

25. A method for delivering a drug into a bodily fluid in a bodily cavity over a period of time, the method comprising the steps of:
  drawing a first volume of the bodily fluid from the bodily cavity through a lumen of a cannula into a hollow member in fluid communication therewith, the hollow member defining at least one lumen for facilitating a unidirectional recirculating flow of fluid therethrough;
  mixing the drug with the bodily fluid in the hollow member to thereby obtain a therapeutic fluid; and
  releasing a first volume of the therapeutic fluid from the hollow member through the lumen of the cannula into the bodily cavity.

26. The method of claim 25, further comprising controllably recirculating the therapeutic fluid through the hollow member.

27. The method of claim 25, wherein the lumen of the cannula is for delivering at least a portion of the therapeutic fluid to a predetermined location in the bodily cavity, the hollow member and the cannula being characterized by flow capacitance and flow resistance selected to obtain a reciprocating flow of the therapeutic fluid through the cannula.

28. The method of claim 26, further comprising altering a concentration of the drug in the therapeutic fluid during recirculation thereof through the hollow member.

29. The method of claim 26 wherein the flow rate of the therapeutic fluid during recirculation through the hollow member is substantially constant.

30. The method of claim 25, further comprising drawing a second volume of the bodily fluid from the bodily cavity.

31. The method of claim 25 wherein the therapeutic fluid comprises a solution of the drug in the bodily fluid.

32. The method of claim 25 wherein the bodily cavity is a human cochlea and the bodily fluid comprises human perilymph.

33. The method of claim 32 further comprising controllably altering fluid pressure within the cochlea.

34. The method of claim 33 wherein fluid pressure within the cochlea is increased by controllably altering the first volume of therapeutic fluid.

* * * * *